United States Patent [19]

Ikeda et al.

[11] Patent Number: 5,795,585

[45] Date of Patent: Aug. 18, 1998

[54] RUMINANT FEED ADDITIVE COMPOSITION CONTAINING NOVEL PHOSPHORIC ACID-AMINO ACID COMPOSITE SALT AND WATER-SOLUBLE HIGH-MOLECULAR SUBSTANCE

[75] Inventors: Toru Ikeda; Toshihide Yukawa, both of Kawasaki, Japan

[73] Assignee: Ajinomoto Co., Inc., Tokyo, Japan

[21] Appl. No.: 777,052

[22] Filed: Dec. 30, 1996

[30] Foreign Application Priority Data

Dec. 28, 1995 [JP] Japan ..................... 7-343163

[51] Int. Cl.$^6$ ..................... A61K 9/16
[52] U.S. Cl. ............. 424/438; 424/442; 424/485; 424/487; 424/488; 424/499; 424/500; 426/2; 426/656
[58] Field of Search ................. 424/442, 438, 424/484–488, 489, 499, 500, 501; 514/776, 777, 76; 426/2, 74, 321, 573, 656

[56] References Cited

U.S. PATENT DOCUMENTS

| 2,473,255 | 6/1949 | Parfentjev ..................... 514/7 |
| 4,351,735 | 9/1982 | Buddemeyer et al. ..................... 252/1 |
| 5,591,443 | 1/1997 | Heinicke ..................... 424/405 |

FOREIGN PATENT DOCUMENTS

| 678246 | 10/1995 | Japan . |
| 2246134 | 1/1992 | United Kingdom . |

*Primary Examiner*—Neil S. Levy
*Attorney, Agent, or Firm*—Oblon, Spivak, McClelland, Maier & Neustadt, P.C.

[57] ABSTRACT

A ruminant feed additive composition comprises a phosphoric acid-amino acid composite salt and a water-insoluble salt of a polyvalent-metal-sensitive water-soluble high-molecular weight substance. The composite salt contains a basic amino acid, an alkaline-earth metal and phosphoric acid, and is insoluble in neutral or alkaline aqueous solution, but is soluble in acidic aqueous solution.

13 Claims, No Drawings

RUMINANT FEED ADDITIVE COMPOSITION CONTAINING NOVEL PHOSPHORIC ACID-AMINO ACID COMPOSITE SALT AND WATER-SOLUBLE HIGH-MOLECULAR SUBSTANCE

BACKGROUND OF THE INVENTION

1. Field of the Invention

The present invention relates to a ruminant feed additive composition. More specifically, the present invention relates to a powdery or granular ruminant feed additive composition which is stable in the rumen of a ruminant and which can release basic amino acids in an abomasum and lower digestive organs of a ruminant.

2. Description of the Background

When biologically active substances, such as amino acids or vitamins are orally administered directly into ruminants, such as cows and sheep, these substances are typically decomposed by microorganisms in the rumen, and are therefore, not effectively utilized. Rumen by-pass preparations which protect these biologically active substances from decomposition by microorganisms in the rumen, but allow them to be digested and absorbed in the abomasum and lower digestive organs, are important in the field of ruminant feed, nutrients and chemicals.

With respect to ruminant feed additives, a method in which a biologically active substance is dispersed in a matrix formed of a hydrophobic substance, such as fats and oils, or a protective substance, such as a basic high-molecular weight substance, and the dispersion is granulated; or a method in which a core containing a biologically active substance is coated with a hydrophobic substance, such as fats and oil, or an acid-sensitive substance, such as a basic high-molecular weight substance, have been proposed.

A method in which the biologically active substance is dispersed in the protective substance includes, for example, Japanese Laid-open Patent Application (Kokai) [hereinafter referred to as "Japanese Kokai"] No. 168,351/1985 which proposes a method which comprises mixing a biologically active substance with at least 20% by weight of calcium carbonate and at least 10% by weight of an aliphatic monocarboxylic acid having 14 or more carbon atoms, hardened fats and oils or the like, and pulverizing the mixture. Another example, Japanese Patent Publication No. 10,780/1984, proposes a method which comprises dispersing from 30 to 50% by weight of a biologically active substance in a protective substance comprising from 10 to 35% by weight of a salt of an aliphatic monocarboxylic acid having from 14 to 22 carbon atoms or ricinoleic acid, and the remainder an aliphatic monocarboxylic acid having from 14 to 22 carbon atoms, ricinoleic acid or hardened fats and oils.

A method in which the biologically active substance is coated with the hydrophobic protective substance includes, for example, Japanese Kokai No. 317,053/1988, which proposes a method in which a biologically active substance is coated with a protective agent composed of an aliphatic monocarboxylic acid having from 12 to 24 carbon atoms, hardened fats and oils, lecithin and a glycerin fatty acid ester.

A method in which the biologically active substance is coated with the acid-sensitive protective substance includes, for example, Japanese Kokai No. 46,823/1979, which proposes a method in which a biologically active substance is coated with a coating composition containing a film-forming basic high-molecular weight substance. Another example, Japanese Kokai No. 217,625/1992, proposes a method in which a biologically active substance is spray-coated with casein in the form of an aqueous emulsion or an aqueous dispersion.

However, in the method in which the biologically active substance is dispersed into the protective substance, the biologically active substance is present near the surface of the particles. Accordingly, for the protective substance to be effective, the content of the biologically active substance has to be notably decreased. Since the residence time of the water-soluble biologically active substance in the rumen is between approximately 10 hours and several days, the biologically active substance is insufficiently protected.

Further, the method in which the biologically active substance-containing core is coated with the acid-sensitive high-molecular weight substance or the hydrophobic protective substance has also been proposed. However, mechanical granulation and/or coating destruction occurs when this composition is mixed or pulverized with another feed composition, and stability in the rumen of a ruminant is impaired in many cases. Thus, the composition is not considered a multi-purpose feed additive.

Preferably, a feed additive can withstand mixing or pulverization with another feed composition, and itself is in the form of a powder or uniform granules and prevent release of the biologically active substance in the rumen, and allows elution of the biologically active substance in the abomasum and lower digestive organs. However, when a basic amino acid is used to improve nutrition of the feed, the phosphorus wolframate of the basic amino-acid is the only substance which contains the basic amino-acid, which takes the form of a powder or uniform granules, and which is insoluble in a neutral solution and is acid-soluble.

Japanese Kokai No. 98,357/1988 discloses a ruminant feed additive composition in which a salt of a basic amino acid and an acidic phosphate is coated. The salt of the acidic phosphoric acid alkaline-earth-metal salt and the basic amino acid of this document corresponds to an analogue of the phosphoric acid-amino acid composite salt of the present invention. However, in the salt of the acidic phosphoric acid alkaline-earth-metal salt and the basic amino acid, the molar ratio of phosphoric acid, alkaline-earth metal and basic amino acid is 1:0.5:1 to 2, which is different from that of the composite salt of phosphoric acid, alkaline-earth metal and basic amino acid of the present invention. The salt of the acidic phosphoric acid alkaline-earth-metal salt and the basic amino acid of the present invention is decomposed in water over the course of time to form an alkaline-earth-metal secondary phosphate, a basic amino-acid primary phosphate or a basic amino-acid secondary phosphate. Since the basic amino-acid phosphate exhibits high water-solubility, this salt is substantially neutral and water-soluble, compared to the solubility of the basic amino acid.

Phosphoric acid forms various salts with alkaline-earth metals, and some of which are insoluble in neutral or alkaline aqueous solutions and are soluble in acidic aqueous solutions. For example, it is known that calcium secondary phosphate, magnesium tertiary phosphate and the like accumulate as scale in equipment for fermentation in industrial plants in which phosphoric acid is often used, causing trouble with the equipment. Ammonium magnesium phosphate shows similar behavior. Only in a prior application (Japanese Patent Application No. 306,385/1994) of the present inventors are disclosed a composite salt comprising 1 mol of phosphoric acid, 1 mol of an alkaline-earth metal and 1 mol of a basic amino acid in which an ammonium ion is replaced with an equivalent basic amino acid as a basic ion; and a tertiary phosphoric acid salt and/or a secondary phosphoric acid salt comprising 1 mol of phosphoric acid, from 1 to 1.45 mols of an alkaline-earth metal and from 1 to 0.1 mols of a basic amino acid.

The present inventors have found that a composite salt of a basic amino acid, an alkaline-earth metal and phosphoric acid is insoluble in a neutral or alkaline aqueous solution and soluble in an acidic aqueous solution, and takes the form of granules. Furthermore, the co-existence of a composite salt obtained by treating the composite salt of the basic amino acid, magnesium and phosphoric acid (hereinafter referred to as "an intermediate starting composite salt") with another divalent or trivalent (polyvalent) metal and a water-insoluble salt of a polyvalent-metal-sensitive water-soluble high-molecular weight substance exhibits a better stability to a neutral or slightly acidic aqueous solution, namely a lower solubility therein, and that it exhibits excellent insolubility in the rumen of the ruminant, and elution in the abomasum and lower digestive organs.

SUMMARY OF THE INVENTION

An objective of the present invention is to provide a safe and economical composition which contains a basic amino acid, which is not dissolved in a rumen of a ruminant, but allows elution of the basic amino acid in an abomasum and lower digestive organs and digestion and absorption with high efficiency, and which takes the form of a powder or uniform granules.

The present invention relates to a ruminant feed additive composition which is composed mainly of a phosphoric acid-amino acid composite salt of a basic amino acid, magnesium, a polyvalent metal other than magnesium and phosphoric acid, represented by formula (1):

$$R_a Mg_b M_c H_d PO_4 \cdot nH_2O \quad (1)$$

wherein

R represents a basic amino-acid hydrogen cation,

M represents a polyvalent metal of m-valence other than magnesium in which m is 2 or 3, a is 0.1 to 1.0, b is 0.85 to 1.43, c is 0.02 to 0.6, d is 0 to 0.3, a+(b×2)+(c×m)+d=3, and n is 0 to 20;

or a phosphoric acid-amino acid composite salt represented by formula (2):

$$R_a Mg_b H_c PO_4 \cdot nH_2O \quad (2)$$

wherein

R represents a basic amino-acid hydrogen cation, a is 0.1 to 1.0, b is 1.0 to 1.45, c is 0 to 0.3, a+(b×2)+c=3, and n is 0 to 20, and a water-insoluble salt of a polyvalent-metal-sensitive water-soluble high-molecular weight substance, which is insoluble in a neutral or alkaline aqueous solution and is soluble in an acidic aqueous solution, and which takes the form of powder or granules. The present invention also relates to a process for producing a ruminant feed additive composition, which comprises mixing a phosphoric acid-amino acid composite salt with a water-insoluble salt of a polyvalent-metal-sensitive water-soluble high-molecular substance, and then bringing the mixture into contact with a divalent or trivalent (polyvalent) metal salt aqueous solution.

DETAILED DESCRIPTION OF THE INVENTION

Examples of phosphoric acid include orthophosphoric acid, condensed phosphoric acids such as diphosphoric acid, tripolyphosphoric acid and trimetaphosphoric acid, and strong phosphoric acid. Salts of phosphoric acid and diphosphoric acid are preferable in view of the solubility. A salt of phosphoric acid is especially preferable. Strong phosphoric acid may be a phosphoric acid which contains no water.

The basic amino acids include natural basic amino acids such as lysine, arginine and ornithine; basic derivatives thereof; and basic derivatives of neutral amino acids. These amino acids are used either singly or in combination. Specific examples include natural basic amino acids such as lysine, arginine and ornithine; and basic derivatives, for example, amides and esters of amino acids such as methionine, tryptophane and threonine.

Examples of the divalent or trivalent (polyvalent) metal other than magnesium include alkaline-earth metals such as calcium, strontium and barium; transition metals such as aluminum, iron, cobalt, manganese and chromium; and other divalent metals such as zinc and cadmium. Salts of calcium, aluminum, iron and zinc are preferable because they are biologically safe.

The phosphoric acid-amino acid composite salt of the present invention is obtained by treating an intermediate starting composite salt with a divalent or trivalent (polyvalent) metal other than magnesium. The intermediate starting composite salt is obtained as a crystalline precipitate when the basic amino acid, magnesium and phosphoric acid are mixed in an aqueous solution under neutral or alkaline conditions in which the basic amino acid is used at a relatively high concentration. A preferable specific example is a salt corresponding to a salt containing a tertiary phosphate of phosphoric acid and/or this tertiary phosphate as a main component, and a secondary phosphate, in which in formula (1) the amount of phosphoric acid is 1 mol, that of the basic amino acid (a) is between 0.1 and 1 mol, that of magnesium (b) is between 0.85 and 1.43 mols, that of the divalent or trivalent (polyvalent) metal of polyvalence (m) other than magnesium is between 0.02 and 0.6 mols, that of the acid residue (d) is between 0 and 0.3 mols, a+(2×b)+(m×c)+d=3, that of the secondary phosphate is ½ or less of that of the tertiary phosphate (molar ratio), and a water content in the composite salt is 30% by weight or less. $H_2O$ may be 0, 1 or 2, but is 0 to 20 depending on the drying conditions. In formula (2), the amount of phosphoric acid is 1 mol, that of the basic amino acid (a) is between 0.1 and 1 mol, that of magnesium (b) is between 1.0 and 1.45 mols, that of the acid residue (c) is between 0 and 0.3 mols, a+(233 b)+c=3, that of the secondary phosphate is ½ or less of that of the tertiary phosphate (molar ratio), and a water content in the composite salt is 30% by weight or less. $H_2O$ may be 0, 1 or 2, but is 0 to 20 depending on the drying conditions.

With respect to the polyvalent-metal-sensitive water-soluble high-molecular weight substance of the present invention, the term "polyvalent-metal-sensitive" means that the water-soluble high-molecular substance or its water-soluble salt is mixed with the polyvalent-metal-containing aqueous solution to form a salt which has a markedly increased viscosity, which gels or which is insoluble in water. The water-insoluble salt of the polyvalent-metal-sensitive water-soluble high-molecular substance which forms the ruminant feed additive composition in combination with the phosphoric acid-amino acid composite salt of the present invention is not particularly limited so long as it is remarkably viscous, gels or is insoluble in water by reaction with the polyvalent metal. This salt includes water-insoluble salts of polysaccharides having a carboxyl group, synthetic high-molecular weight substances and proteins. Examples of the polysaccharides having the carboxyl group include alginic acid, gellan gum, pectin, carboxymethyl cellulose and carboxymethyl starch. Examples of the high-molecular weight substances include polyacrylic acid and/or a copolymer of polyacrylic acid, and polymethacrylic acid and/or a copolymer of polymethacrylic acid. Examples of the proteins include soybean protein and casein. As the polyvalent metal salt, a calcium salt, an aluminum salt, a zinc salt and an iron salt are especially preferable.

A process for producing the phosphoric acid-amino acid composite salt of the present invention is not particularly limited so long as the salt is insoluble in a neutral or alkaline aqueous solution and is soluble in an acidic aqueous solution. These salts will have a lower solubility in a neutral or alkaline aqueous solution than in an acidic solution. Preferable is a process in which the intermediate starting composite salt comprising phosphoric acid, magnesium and the basic amino acid, represented by formula (2), is mixed with a solution of a salt of a divalent or trivalent (polyvalent) metal other than magnesium, and the mixture is separated and dried.

There are four processes for producing the intermediate starting composite salt. In the first process, a secondary phosphate of magnesium is dispersed into a large amount of a basic aqueous solution of a basic amino acid, the dispersion is heated, and the resulting precipitate is washed. Specifically, magnesium hydrogenphosphate is added to a large amount of a basic concentrated aqueous solution of a basic amino acid formed through treatment with an ion-exchange resin, and the mixture is heated and stirred. Magnesium hydrogenphosphate in the mixed solution dissolves over time, and the phosphoric acid-amino acid composite salt is formed as a precipitate. The precipitate is subjected to solid-liquid separation. The excess basic amino acid on the precipitate is washed away with water, and the residue is dried to form the intermediate starting composite salt.

In the second process, an aqueous solution of a magnesium salt and phosphoric acid are mixed at a molar ratio of 1.0 to 1.45:1.0 in a large amount of a basic aqueous solution of a basic amino acid, and the resulting precipitate is washed. Specifically, 3 mols or more of a basic concentrated aqueous solution of a basic amino acid are neutralized with 1 mol of phosphoric acid to form a high concentration tertiary phosphate solution. Then, from 1.0 to 1.45 mols of a concentrated aqueous solution of a neutral magnesium salt, such as magnesium chloride and/or magnesium sulfate, are added and the mixture is stirred. The resulting precipitate is subjected to solid-liquid separation. The excess basic amino acid on the precipitate is washed away with water, and the residue is dried to form the intermediate starting composite salt.

In the third process, a basic aqueous solution of a basic amino acid is mixed and neutralized with phosphoric acid at a molar ratio of 1.0:1.0. This solution is mixed with 1.0 to 1.45 mols of magnesium hydroxide and/or magnesium oxide, and the resulting precipitate is washed. Specifically, 1.0 mol of a concentrated basic aqueous solution of a basic amino acid is mixed and neutralized with 1.0 mol of phosphoric acid. The concentrated aqueous solution of the basic amino-acid primary phosphate is mixed with an aqueous dispersion of from 1.0 to 1.45 mols of magnesium hydroxide and/or magnesium oxide. The excess basic amino acid on the precipitate is washed away with water, and the residue is dried to form the intermediate starting composite salt.

In the fourth process, a basic aqueous solution of a basic amino acid is mixed and neutralized with phosphoric acid at a molar ratio of 0.1 to 0.8:1.0. This solution is mixed with from 1.1 to 1.45 mols of magnesium hydroxide and/or magnesium oxide, and the mixture is then heat-dried. Specifically, from 0.1 to 0.8 mols of a concentrated basic aqueous solution of a basic amino acid are mixed and neutralized with 1.0 mol of phosphoric acid. The concentrated mixed aqueous solution is mixed with an aqueous dispersion of from 1.1 to 1.45 of magnesium hydroxide and/or magnesium oxide, and the resulting precipitate is dried to form the intermediate starting composite salt.

In these four processes, the basic concentrated aqueous solution of the basic amino acid is used as a starting material, and the amino-acid composite salt is formed by a reaction in which the basic amino acid is used at a relatively high concentration. In the present invention, the concentration of the basic amino acid is preferably between 10 and 60 parts by weight per 100 parts by weight of the total water content present in the reaction system, in the case of the second process in which the highest concentration is selected, and is preferably 3 to 20 parts by weight per 100 parts by weight of the total water content present in the reaction system, in the case of the fourth process in which the lowest concentration is selected.

These four processes can also be used in combination. Specific examples include a process in which an appropriate amount of a concentrated aqueous solution of a neutral salt of phosphoric acid and/or magnesium is added to a reaction solution in which the magnesium phosphate-amino acid composite salt is formed as a precipitate in the first process, these are mixed while being stirred, and the mixture is heated, whereby the concentrated aqueous solution is reacted with the large amount of basic amino acid remaining in the reaction solution. Another specific example is a process in which an appropriate amount of magnesium hydroxide is added to a reaction solution in which a magnesium phosphate-amino acid composite salt is formed as a precipitate in the second process, whereby magnesium hydroxide is reacted with large amounts of the basic amino acid and phosphoric acid remaining in the reaction solution.

In the present invention, the salt solution of the divalent or trivalent (polyvalent) metal other than magnesium, which is used when treating the intermediate starting composite salt, is not particularly limited. Preferable, a weakly acidic or basic aqueous solution or dispersion containing at least 0.001 parts by weight, per 100 parts by weight of the solution, of the polyvalent metal ion other than magnesium is used. Specific examples thereof include aqueous solutions of aluminum salts such as aluminum chloride, polyaluminum chloride, aluminum sulfate, ammonium alum and potassium alum; aqueous solutions or aqueous dispersions of calcium salts such as calcium chloride, calcium sulfate, calcium hydroxide and calcium nitrate; aqueous solutions of iron salts such as ferrous chloride, ferric chloride, ferrous sulfate, ferric sulfate, potassium iron sulfate and ammonium iron sulfate; and aqueous solutions or aqueous dispersions of zinc salts such as zinc chloride, ammonium zinc chloride and zinc hydroxide. These solutions of polyvalent metals other than magnesium may be used either singly or in combination as a mixed salt solution or a composite salt solution.

The necessary amount of the divalent or trivalent (polyvalent) metal salt other than magnesium, which is used to treat the intermediate starting composite salt of the present invention, varies depending on the time of contact with the intermediate starting composite salt, the concentration of the divalent or trivalent (polyvalent) metal salt other than magnesium, and the concentration of the intermediate starting composite salt dispersion. However, since most of the divalent or trivalent (polyvalent) metal ions other than magnesium migrate into the desired composite salt, the concentration of this metal salt is preferably 0.02 to 0.6 mols per mol of phosphoric acid in the intermediate starting composite salt.

In this invention, a method of obtaining a composition comprising a phosphoric acid-amino acid composite salt and a polyvalent-metal-sensitive water-soluble high-molecular weight substance is not particularly limited. Preferable are: (i) a method in which the composite salt is prepared, and then mixed with an aqueous solution of an alkali-metal salt and/or an ammonium salt of a polyvalent-metal-sensitive water-soluble high-molecular weight substance, and the mixture is dried; and (ii) a method in which an intermediate starting composite salt is mixed with an aqueous solution of an alkali-metal salt and/or an ammonium salt of a polyvalent-metal-sensitive water-soluble high-molecular weight substance, and the mixture is then brought into contact with a salt solution of a divalent or trivalent (polyvalent) metal other than magnesium, then separated and dried as required.

In the present invention, when the composition comprising the phosphoric acid-amino acid composite salt and the water-insoluble salt of the polyvalent-metal-sensitive water-soluble high-molecular weight substance is used as a ruminant feed additive composition, the insolubility of the intermediate starting composite salt increases in neutral or alkaline aqueous solution, and the intermediate starting composite salt is sometimes even insoluble in a neutral buffer aqueous solution, while the solubility in acidic aqueous solution is further increased. That is, when the phosphoric acid-amino acid composite salt obtained by treating the intermediate starting composite salt with the divalent or trivalent (polyvalent) metal other than magnesium of the present invention is brought together with the water-insoluble salt of the polyvalent-metal-sensitive water-soluble high-molecular weight substance, a surface layer of the water-insoluble salt of the polyvalent-metal-sensitive water-soluble high-molecular weight substance is formed on the surface of the phosphoric acid-amino acid composite salt of the present invention. Consequently, a composition which is insoluble in a neutral buffered aqueous solution, and which is soluble in an acidic buffered aqueous solution, is formed.

The composition of the phosphoric acid-amino acid composite salt and the water-insoluble salt of the polyvalent-metal-sensitive water-soluble high-molecular weight substance has the remarkable property of being insoluble in neutral or alkaline aqueous solution and being soluble in acidic aqueous solution. Accordingly, this composition is stable in the neutral rumen, and is completely dissolved in the acidic abomasum, releasing the basic amino acids which are absorbed in the small intestine. The composition of the present invention can be utilized as a powdery ruminant feed additive composition in which the basic amino acid that is an active ingredient effectively protected in the rumen from decomposition by microorganisms, yet is digested and absorbed in the abomasum and lower digestive organs.

The composition comprising the composite salt and the water-insoluble salt of the polyvalent-metal-sensitive water-soluble high-molecular weight substance is dried, and pulverized, and the powder is used as is. Alternatively, the composition may be used as a ruminant feed additive composition in the form of granules which have not been pulverized, or in the form of granules having an appropriate diameter.

In the present invention, the granules of the phosphoric acid-amino acid composite salt are preferably uniform granules. The uniform granules of the present invention may have a diameter of from approximately 1 to 2 mm. The limit of the diameter in which granules are destroyed through chewing is approximately 1 to 2 mm. Therefore, when the composition of the granular material having a diameter of from approximately 1 to 2 mm is uniform, the composition of the granules after chewing is not changed. Thus, when the granules are mixed or pulverized with the other feed components, the elution of the basic amino-acid component is not greatly changed.

The granulation can be conducted by any typical method, so long as the granules have a uniform composition. Preferable are: (i) a method in which the composite salt is mixed with an appropriate binder, and the mixture is granulated through extrusion-granulation, rolling-granulation, compression-granulation, melt-spray-granulation or the like; (ii) a method in which a slurry is spray-dried; and (iii) a method in which a powder is granulated together with an appropriate binder through granulation using a fluidized bed or through stirring-granulation.

The binder is not particularly limited, and an ordinary binder can be used. The binder includes water-soluble binders and hydrophobic binders. Specific examples of the water-soluble binders include water-soluble polysaccharides such as a starch, a carboxymethyl cellulose salt, an alginate, hydroxypropyl cellulose and a starch glycolic acid salt; water-soluble proteins such as casein sodium, gelatin and soybean protein; saccharides such as molasses, lactose and dextrin; and synthetic high-molecular substances such as a polymethacrylate salt, polyvinyl alcohol and polyvinyl pyrrolidone. Specific examples of the hydrophobic binders include natural waxes such as a shellac resin, a rosin, bees wax and paraffin wax; higher aliphatic acids such as cetanol and stearic acid; materials associated with fats and oils, such as higher fatty acid metal salts, animal and vegetable fats and oils, and hardened animal and vegetable fats and oils; nonionic surfactants such as glycerin monostearate; and semi-synthetic resins and synthetic high-molecular substances such as acetyl cellulose, polyvinyl acetate, ester gum and a coumarone resin.

The ratio of the binder to the phosphoric acid-amino acid composite salt which undergoes granulation varies depending on the type of binder, and is preferably 0.1 to 50% by weight per 100 parts by weight of the phosphoric acid-amino acid composite salt. Further, the diameter of the granules is not particularly limited. Granules having an average diameter of approximately 5 mm or less are preferred, because they allow for a less irregular feed. Granules having an average diameter of from 2 to 0.2 mm are especially preferred, because they facilitate mixing with other feed components.

Granules containing the phosphoric acid-amino acid composite salt of the present invention can be prepared by adding, besides the amino-acid composite salt and the binder, other additives, in order to adjust the specific gravity, to increase the strength of the granules, to increase melt-destruction in the abomasum, to improve processability in preparation of the granules, and so forth. The additives are selected from powders and waxes to form granules. Specific examples include inorganic substances such as carbonates, phosphates and hydroxides of alkaline-earth metals, talc, clay, bentonite and fine silica; and organic substances such as paraffin wax, polyethylene powder, pulp powder, cellulose powder and xanthone.

In addition, granules containing the phosphoric acid-amino acid composite salt of the present invention may be prepared by uniformly dispersing with another biologically active substance which does not impair the protection of the phosphoric acid-amino acid composite salt in the rumen, and elution in the abomasum. The other biologically active substance may include known nutrients and chemicals such as amino acids, derivatives thereof, hydroxy compounds of amino acids, vitamins and veterinary agents. These may be used either singly or in combination. Specific examples include amino acids such as methionine, tryptophan and threonine; amino-acid derivatives such as calcium salts of N-acylamino acid and N-hydroxymethyl methionine; amino-acid hydroxy compounds such as 2-hydroxy-4-methylmercaptobutyric acid and its salt; calory sources such as starch, fatty acid and fatty acid metal salt; vitamins such as vitamin A, vitamin A acetate, vitamin A palmitate, B vitamins, thiamine, thiamine hydrochloride, riboflavin, nicotinic acid, nicotinic acid amide, calcium panthotenate, choline panthotenate, pyridoxine hydrochloride, choline chloride, cyanocobalamin, biotin, folic acid, p-aminobenzoic acid, vitamin $D_2$, vitamin $D_3$ and vitamin E, as well as substances having the similar properties; tetracycline-type, amino-macrolide-type, macrolide-type and polyether-type antibiotics; insect repellents such as negphon; vermifuges such as piperazine; and hormones such as estrogen, stilbestrol, hexestrol, thyroprotein, goitrogen and growth hormone.

The present invention is illustrated more specifically by referring to the following Examples and Comparative Examples. However, the present invention is not limited thereto.

With respect to a biologically active substance, an amount of an amino acid and an amount of an amino acid eluted in the Examples were measured through liquid chromatography.

EXAMPLES

Elution Into Pure Water

One gram of the sample prepared was charged into a 200-milliliter Erlenmeyer flask, and 100 ml of pure water were poured therein. The solution was sonicated at room temperature for 10 minutes. Subsequently, the amount of elution of a basic amino acid was analyzed, and elution into pure water was calculated.

Protection in a Corresponding Rumen Solution

Approximately 0.5 g of the sample prepared were charged into a 300-milliliter Erlenmeyer flask, and 200 ml of a McDougall buffer solution corresponding to a rumen solution was poured therein. The mixed solution was shaken at 39° C. for 24 hours. After the completion of the shaking, the amount of a basic amino acid eluted was analyzed, and protection in the corresponding rumen solution was calculated.

Protection in a Corresponding Rumen Solution in the Administration of a Small Amount of a Sample Approximately 0.2 g of the sample prepared were charged into a 300-milliliter Erlenmeyer flask, and 200 ml of a McDougall buffer solution corresponding to the rumen solution was poured therein. The mixed solution was shaken at 39° C. for 24 hours. After the completion of the shaking, the amount of a basic amino acid eluted was analyzed, and protection in the corresponding rumen solution in the administration of the small amount of the sample was calculated.

McDougall buffer solution:

Buffer solution obtained by dissolving the following reagents into 1,000 ml of water

| | |
|---|---|
| sodium hydrogencarbonate | 7.43 g |
| disodium hydrogenphosphate 12-hydrate | 7.00 g |
| sodium chloride | 0.34 g |
| potassium chloride | 0.43 g |
| magnesium chloride 6-hydrate | 0.10 g |
| calcium chloride | 0.05 g |

Elution Into a Corresponding Abomasum Solution

Approximately 0.5 g of the sample prepared were charged into a 300-milliliter Erlenmeyer flask, and 200 ml of an acetate-phosphate buffer solution corresponding to an abomasum solution was poured therein. The mixed solution was shaken at 39° C. for 1 hour. After the completion of the shaking, the amount of a basic amino acid eluted was analyzed, and the elution into the corresponding abomasum solution was calculated.

Acetate-phosphate buffer solution:

Buffer solution prepared by dissolving the following reagents into 1,000 ml of water and adjusting the pH of the solution to 2.2 with hydrochloric acid.

| | |
|---|---|
| sodium dihydrogenphosphate 2-hydrate | 1.95 g |
| sodium acetate 3-hydrate | 3.40 g |

Example 1

Magnesium secondary phosphate 3-hydrate (174.3 g) was added to 1,300 g of an L-lysine basic aqueous solution (concentration: 45% by weight), and the mixture was heat-stirred at 80° C. for 3 hours. Then, particulate crystals of magnesium secondary phosphate 3-hydrate dissolved, and fine crystals were formed in large amounts. The thus-formed crystals were filtered, washed with 1,000 ml of water, and then dried at 60° C. under reduced pressure to obtain 285 g of a white crystalline powder. One gram of this white powder was added to 100 ml of each of pure water and the corresponding rumen solution, and the mixtures were stirred. No dissolution was observed. This product was designated intermediate starting composite salt-1.

Example 2

An L-lysine basic aqueous solution (4,386 g, concentration: 20% by weight) was mixed and neutralized with 231 g of phosphoric acid (concentration: 85%). To this mixed solution was added a solution of 493 g of magnesium sulfate 7-hydrate in 1,000 ml of water, all at once. The gel-like precipitate formed was filtered, washed with 1,200 ml of water, and then dried at 60° C. under reduced pressure to give 280 g of a white powder. One gram of this white powder was added to 100 ml of each of pure water and the corresponding rumen solution, and the mixtures were stirred. No dissolution was observed. This product was designated intermediate starting composite salt-2.

Example3

An L-lysine basic aqueous solution (650 g, concentration: 45% by weight) was mixed and neutralized with 461.2 g of phosphoric acid (concentration: 85%). The resulting solution was mixed with a dispersion obtained by fully dispersing 291.7 g of magnesium hydroxide in 1,000 ml of water. Then, the mixture was allowed to react, and generate heat, to form a white solid. After this white solid was heated at 95° C. for 3 hours, 3,000 ml of pure water were added, and the mixture was pulverized. The solid material was filtered, washed with 3,000 ml of water, and dried at 60° C. under reduced pressure to obtain 750 g of a white powder. One gram of this white powder was added to 100 ml of each of pure water and the corresponding rumen solution, and the mixtures were stirred. No dissolution was observed. This product was designated intermediate starting composite salt-3.

Example 4

An L-lysine basic aqueous solution (311 g, concentration: 47% by weight) was mixed and neutralized with 461.2 g of phosphoric acid (concentration: 85%). The resulting solution was mixed with a dispersion obtained by fully dispersing 291.7 g of magnesium hydroxide in 700 ml of water. Then, the mixture was allowed to react, and generate heat, to form a white solid. This white solid was heated at 90° C. for 3 hours, then pulverized, and dried at 60° C. under reduced pressure to obtain 750 g of a white powder. One gram of this white powder was added to 100 ml of each of pure water and the corresponding rumen solution, and the mixtures were stirred. No dissolution was observed. This product was designated intermediate starting composite salt-4.

Example 5

An L-lysine basic aqueous solution (4,386 g, concentration: 20% by weight) was mixed and neutralized with 231 g of phosphoric acid (concentration: 85%), and 20 g of the white crystalline powder obtained in Example 1 were added thereto. When a solution of 407 g of magnesium chloride 6-hydrate in 500 ml of water was gradually added to the solution in small portions, fine crystals were formed. The resulting crystals were filtered, washed with 3 liters of water, and dried at 60° C. under reduced pressure to obtain 573 g of a white crystalline powder. One gram of this white powder was added to 100 ml of each of pure water and the corresponding rumen solution, and the mixtures were stirred. No dissolution was observed. This product was designated intermediate starting composite salt-5.

Example 6

Magnesium secondary phosphate 3-hydrate (87.2 g) was added to 730 g of an L-lysine basic aqueous solution (concentration: 40% by weight), and the mixture was heat-stirred at 80° C. for 3 hours. Consequently, particulate crystals of magnesium secondary phosphate 3-hydrate dissolved, and fine crystals were formed. After 46.1 g of phosphoric acid (concentration: 85%) were gradually added to this mixture while being cooled, a solution of 98.6 g of magnesium sulfate 7-hydrate in 150 ml of water was added, all at once. The mixture then became a viscous crystalline slurry. The resulting crystals were filtered, washed with 1,300 ml of water, and then dried at 60° C. under reduced pressure to obtain 198 g of a white crystalline powder. One gram of this white powder was added to 100 ml of each of pure water and the corresponding rumen solution, and the mixtures were stirred. No dissolution was observed. This product was designated intermediate starting composite salt-6.

Example 7

An L-lysine basic aqueous solution (4,873 g, concentration: 30% by weight) was mixed and neutralized with 461 g of phosphoric acid (concentration: 85%). To this mixture was added a solution of 610 g of magnesium chloride 6-hydrate in 1 liter of water, all at once. The viscous mixture formed was uniformly mixed with a dispersion obtained by dispersing 93.3 g of magnesium hydroxide in 700 ml of water, and the resulting mixed solution was allowed to stand overnight to form a white precipitate. The precipitate was filtered, washed with 7,000 ml of water, and then dried at 60° C. under reduced pressure to obtain 980 g of a white powder. One gram of this white powder was added to 100 ml of each of pure water and the corresponding rumen solution, and the mixtures were stirred. No dissolution was observed. This product was designated intermediate starting composite salt-7.

Example 8

Each (250 g) of the intermediate starting composite salts-1 to -3 obtained in Examples 1 to 3 was mixed with 40 g of calcium chloride 2-hydrate and 2,000 ml of water, and the mixture was stirred at room temperature for 2 hours. After the solid material was separated from the mixed solution through filtration, 300 ml of water and 3.0 g of carboxymethyl cellulose sodium salt were added. These were mixed well, and the mixture was dried to obtain from 252 g to 241 g of each of desired compositions-1 to -3 comprising the composite salt and carboxymethyl cellulose calcium salt.

Example 9

The intermediate starting composite salt-4 (250 g) obtained in Example 4 was mixed with 3.0 g of sodium alginate and 350 ml of water, and the mixture was extruded into a solution of 20 g of calcium chloride in 1,000 ml of water using a syringe. The mixture which solidified in string form was further dipped therein at room temperature for 2 hours, then washed with water, and dried to give 247 g of desired composition-4 comprising the composite salt and calcium alginate.

Example 10

One hundred grams of each of the intermediate starting composite salts -5 and -6 obtained in Examples 5 and 6 were mixed with 20 g of zinc chloride and 1,000 ml of water, and the mixture was stirred at room temperature for 3 hours. After the solid material was separated from the mixture through filtration, 200 ml of water and 3.0 g of pectin were added thereto. These were mixed well, and the mixture was then dried to give from 102 to 100 g of each of desired compositions -5 and -6 comprising the composite salt and pectin zinc salt.

Example 11

One hundred grams of the intermediate starting composite salt-7 obtained in Example 7 were mixed with 1,000 ml of water, and 30 g of ammonium aluminum sulfate (burnt alum) were added. The mixture was stirred at room temperature for 2 hours. After the solid material was separated from the mixture through filtration, 200 ml of water and 2.0 g of sodium polyacrylate were added. These were mixed well, and the mixture was then dried to give 103 g of desired composition-7 comprising the composite salt and aluminum polyacrylate.

Example 12

With respect to the intermediate starting composite salts-1 to -7 as obtained in Examples 1 to 7 and compositions-1 to -7 comprising the composite salts and the water-insoluble salts of the polyvalent-metal-sensitive water-soluble high-molecular weight substances as obtained in Examples 8 to 11, the lysine content, the Mg content and the contents of polyvalent metals other than magnesium were measured. The results are shown in Table 1. The lysine content was analyzed through liquid chromatography by dissolving a sample in dilute hydrochloric acid. The Mg content was measured through ICP (inductivity coupled plasma) emission spectral analysis. Further, the rate of elution into pure water, the protection in a corresponding rumen solution, the protection in a corresponding rumen solution when administering a small amount of a sample, and elution into a corresponding abomasum solution, are also shown in Table 1.

heated at 95° C. for 3 hours, and 1,000 ml of pure water were added. The mixture was pulverized, and 10 g of calcium hydroxide were added. The resulting mixture was stirred for 2 hours. The solid material was filtered, and washed with 1,000 ml of water. Subsequently, 500 ml of water and 3.0 g of sodium alginate were added. They were mixed well, and the mixture was then dried to obtain 245 g of a powder of a desired composition comprising the composite salt and calcium alginate. One gram of this powder was added to 100 ml of each of pure water and the corresponding rumen solution, and the mixtures were stirred. No dissolution was observed. One gram of this powder was dissolved in 100 ml of dilute hydrochloric acid, and the concentration of arginine was measured. As a result, it was found to be 345 mg/dl, and the content of arginine was 34.5%. Further, 1.00 g of this white powder was mixed with 100 ml of pure water, and the mixture was sonicated for 5 minutes. Then, the concentration of arginine in the supernatant was measured. It was found to be 30 mg/dl, and the rate of elution into pure water

TABLE 1

Analysis of amino-acid composite salt composition and properties thereof (unit: wt. %)

| Intermediate starting composite salt | 1 | 2 | 3 | 4 | 5 | 6 | 7 |
|---|---|---|---|---|---|---|---|
| Lysine content | 51.1 | 20.0 | 18.5 | 19.5 | 50.4 | 36.5 | 29.8 |
| Mg content | 8.5 | 15.4 | 16.6 | 16.2 | 8.4 | 11.8 | 13.4 |
| Phosphorous content (as $PO_4$) | 10.8 (33.1) | 14.8 (45.4) | 15.8 (48.5) | 16.5 (50.6) | 10.7 (32.8) | 12.7 (39.0) | 13.5 (41.4) |
| Elution into pure water | 84.2% | 13.0% | 35.0% | 48.7% | 86.2% | 55.3% | 38.5% |
| Protection in rumen | 10% | 85% | 55% | 42% | 9% | 40% | 57% |
| Protection in rumen in administering small amount | 5% | 65% | 35% | 26% | 4% | 20% | 38% |
| Elution into abomasum | 100% | 100% | 100% | 100% | 100% | 100% | 100% |

| Composition No. | 8-1 | 8-2 | 8-3 | 9-4 |
|---|---|---|---|---|
| *1 | carboxymethyl cellulose Ca salt | carboxymethyl cellulose Ca salt | carboxymethyl cellulose Ca salt | calcium alginate |
| Lysine content | 46.0 | 18.1 | 17.0 | 18.4 |
| Mg content | 7.4 | 14.7 | 15.0 | 15.7 |
| Polyvalent metal other than Mg Content | Ca 2.6 | Ca 2.0 | Ca 3.6 | Ca 4.0 |
| Phosphorus content (as $PO_4$) | 10.8 (33.1) | 14.7 (45.0) | 15.7 (48.1) | 16.8 (51.5) |
| Elution into pure water | 63.2% | 6.0% | 32.0% | 37.7% |
| Protection in rumen | 32% | 92% | 58% | 52% |
| Protection in rumen in administering small amount | 31% | 89% | 55% | 50% |
| Elution into abomasum | 100% | 100% | 100% | 99% |

Example 13

L-arginine (174.2 g) and 98.0 g of phosphoric acid (concentration: 85%) were dissolved in 300 ml of water, and the solution was mixed with a dispersion obtained by dispersing 72.9 g of magnesium hydroxide in 200 ml of water. Consequently, the mixture was allowed to react, and generate heat, to form a white solid. This white solid was was 8.7%. Protection of the white powder in the corresponding rumen solution and elution thereof into the corresponding abomasum solution were evaluated. As a result, the rate of protection in the corresponding rumen solution was 12%, and the rate of elution into the corresponding abomasum solution was 100%.

Example 14

Two-hundred grams of composition-1 comprising the composite salt and carboxymethyl cellulose calcium salt as obtained in Example 8 were mixed with 150 g of a hardened soybean oil. Then, the mixture was heat-extruded at 65° C. through a die having a bore diameter of 1 mm using a heat-extrusion machine, and was cut to a length of approximately 1 mm to form granules having a diameter of approximately 1 mm. With respect to the resulting granules, protection in the corresponding rumen solution and elution into the corresponding abomasum solution were evaluated. Consequently, the rate of protection in the corresponding rumen solution was 80%, and the rate of elution into the corresponding abomasum solution was 90%.

Example 15

Two-hundred grams of composition-4 comprising the composite salt and calcium alginate as obtained in Example 9 were mixed with 15 g of methionine powder, 40 g of calcium carbonate, 20 g of casein sodium and 4 g of starch sodium glycolate and 70 ml of water were added. The resulting mixture was kneaded, extruded using a disc pelletizer having a bore diameter of 2 mm, cut to a length of approximately 2 mm, and dried to form granules having a diameter of approximately 2 mm. The thus-obtained granules were further cut into smaller granules having a diameter of approximately 0.5 mm. The five granules thereof were heat-extracted with dilute hydrochloric acid, and the amino-acid content was measured. As a result, no difference in the amino-acid content was observed among these smaller granules. With respect to the thus-obtained granules, protection in the corresponding rumen solution and elution into the corresponding abomasum solution were evaluated. Consequently, the rate of protection of lysine in the corresponding rumen solution was 99%, and that of protection of methionine in the corresponding rumen solution was 67%. The rates of elution of lysine and methionine into the corresponding abomasum solution were both 95%. Further, with respect to the smaller granules having the diameter of approximately 0.5 mm, protection in the corresponding rumen solution and elution into the corresponding abomasum solution were also evaluated. Consequently, the rate of protection of lysine in the corresponding rumen solution was 98%, and that of protection of methionine in the corresponding rumen solution was 64%. The rates of elution of lysine and methionine into the corresponding abomasum solution were both 98%.

Effects of the Invention

As stated above, in the present invention, a ruminant feed additive composition which contains a basic amino acid such as lysine or the like that tends to be lacking in a ruminant feed, which is excellent in terms of protection in a rumen and elution in an abomasum can be formed from a composition which contains a composite salt obtained by treating a composite salt of a basic amino acid, magnesium and phosphoric acid with a divalent or trivalent (polyvalent) metal other than magnesium, with a water-insoluble salt of a polyvalent-metal-sensitive water-soluble high-molecular weight substance, and which is insoluble in a neutral or alkaline aqueous solution and is soluble in an acidic aqueous solution. The granules of the present invention are less influenced by destruction of the granules owing to chewing or mixing with other feed components. Thus, the present invention can provide a ruminant feed additive composition which is excellent in terms of protection in a rumen and elution in an abomasum in comparison with the prior art.

The present invention is to provide a feed additive composition which enables a biologically active substance to be effectively absorbed into a ruminant. Thus, it is extremely industrially significant.

Obviously, numerous modifications and variations of the present invention are possible in light of the above teachings. It is therefore to be understood that within the scope of the appended claims, the invention may be practiced otherwise than as specifically described herein.

The priority document of the present application, Japanese Patent Application No. 343 163/1995, filed on Dec. 28, 1995, is hereby incorporated by reference.

What is claimed as new and desired to be secured by Letters Patent of the United States is:

1. A ruminant feed additive in powder or granular form, comprising:
   (i) a water-insoluble salt of a water-soluble polymeric substance that gels or is insoluble in water when reacted with a polyvalent metal, wherein the water-insoluble salt is at least one member selected from the group consisting of a calcium salt, an aluminum salt, a zinc salt and an iron salt of alginic acid, carrageenan, gellan gum, pectin, carboxymethyl cellulose, carboxymethyl starch, polyacrylic acid, a polyacrylic acid copolymer, polymethacrylic acid, a polymethacrylic acid copolymer, soybean protein or casein, and
   (ii) a phosphoric acid-amino acid composite salt represented by formula (1):

$$R_a Mg_b M_c H_d PO_4 \cdot nH_2O \tag{1}$$

wherein

R represents a basic amino-acid hydrogen cation,

M represents a polyvalent metal of m-valence other than magnesium, m is 2 or 3, a is 0.1 to 1.0, b is 0.85 to 1.43, c is 0.02 to 0.6, d is 0 to 0.3, a+(b×2)+(c×m)+d=3, and n is 0 to 20, wherein said ruminant feed additive is stable in the rumen of a ruminant and is capable of releasing basic amino acids in an abomasum and lower digestive organs of a ruminant.

2. The ruminant feed additive of claim 1, wherein the basic amino-acid hydrogen cation is a hydrogen cation of lysine or arginine, or mixture thereof.

3. The ruminant feed additive of claim 1, wherein the polyvalent metal other than magnesium is at least one member selected from the group consisting of calcium, aluminum, zinc and iron.

4. The ruminant feed additive of claim 1, wherein said ruminant feed additive is more soluble in acidic aqueous solution than in neutral or basic aqueous solution.

5. A process for producing a ruminant feed additive in powder or granular form, comprising:
   mixing a phosphoric acid-amino acid composite salt with an aqueous solution of a water-soluble salt of a water-soluble polymeric substance that gels or is insoluble in water when reacted with a polyvalent metal, to form a mixture; wherein the water-soluble polymeric substance is at least one member selected from the group consisting of alginic acid, carrageenan, gellan gum, pectin, carboxymethyl cellulose, carboxymethyl starch, polyacrylic acid, a polyacrylic acid copolymer, polymethacrylic acid, a polymethacrylic acid copolymer, soybean protein or casein, and drying the mixture;

wherein the phosphoric acid-amino composite salt is represented by formula (1):

$$R_aMg_bM_cH_dPO_4 \cdot H_2O \qquad (1)$$

wherein

R represents a basic amino-acid hydrogen cation,

M represents a polyvalent metal of m-valence other than magnesium, m is 2 or 3, a is 0.1 to 1.0, b is 0.85 to 1.43, c is 0.02 to 0.6, d is 0 to 0.3, a+(b×2)+(c×m)+d =3, and n is 0 to 20, wherein said ruminant feed additive is stable in the rumen of a ruminant and is capable of releasing basic amino acids in an abomasum and lower digestive organs of a ruminant.

6. A process for producing a ruminant feed additive in powder or granular form, comprising:

mixing a phosphoric acid-amino acid composite salt with an aqueous solution of a water-soluble salt of a water-soluble polymeric substance that gels or is insoluble in water when reacted with a polyvalent metal, to form a mixture; wherein the water-soluble polymeric substance is at least one member selected from the group consisting of alginic acid, carrageenan, gellan gum, pectin, carboxymethyl cellulose, carboxymethyl starch, polyacrylic acid, a polyacrylic acid copolymer, polymethacrylic acid, a polymethacrylic acid copolymer, soybean protein or casein, and contacting said mixture with an aqueous solution of a divalent or trivalent metal salt;

wherein the amino-acid composite salt is represented by the formula (2):

$$R_aMg_bH_cPO_4 \cdot nH_2O \qquad (2)$$

wherein

R represents a basic amino-acid hydrogen cation, a is 0.1 to 1.0, b is 1.0 to 1.45, c is 0 to 0.3, a+b×2+c=3, to n is 0 to 20, wherein said ruminant feed additive is stable in the rumen of a ruminant and is capable of releasing basic amino acids in an abomasum and lower digestive organs of a ruminant.

7. The ruminant feed additive of claim 1, wherein said ruminant feed additive is in the form of granules.

8. The ruminant feed additive of claim 1, further comprising another biologically active substance.

9. A ruminant feed additive prepared by the process of claim 5.

10. A ruminant feed additive prepared by the process of claim 6.

11. The process of claim 5, wherein the basic amino-acid hydrogen cation is a hydrogen cation of lysine or arginine, or mixture thereof.

12. The process of claim 6, wherein the basic amino-acid hydrogen cation is a hydrogen cation of lysine or arginine, or mixture thereof.

13. The process of claim 5, wherein the polyvalent metal other than magnesium is at least one member selected from the group consisting of calcium, aluminum, zinc and iron.

* * * * *